US012765614B2

(12) United States Patent

Mukhopadhyay et al.

(10) Patent No.: US 12,765,614 B2
(45) Date of Patent: Oct. 20, 2026

(54) METHOD AND SYSTEM TO ESTIMATE SMOKING EPISODES FROM SMOKE PUFFS USING A WEARABLE DEVICE

(71) Applicant: Tata Consultancy Services Limited, Mumbai (IN)

(72) Inventors: Shalini Mukhopadhyay, Kolkata (IN); Varsha Sharma, Kolkata (IN); Swarnava Dey, Kolkata (IN); Sakyajit Bhattacharya, Kolkata (IN); Avik Ghose, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 391 days.

(21) Appl. No.: 18/542,846

(22) Filed: Dec. 18, 2023

(65) Prior Publication Data

US 2024/0225134 A1 Jul. 11, 2024

(51) Int. Cl.

| | |
|---|---|
| ***G16H 50/00*** | (2018.01) |
| ***A24F 47/00*** | (2020.01) |
| ***A61B 5/00*** | (2006.01) |
| ***A61B 5/08*** | (2006.01) |
| ***A61B 5/107*** | (2006.01) |

(Continued)

(52) U.S. Cl.

CPC ............ *A24F 47/00* (2013.01); *A61B 5/0022* (2013.01); *A61B 5/0806* (2013.01); *A61B 5/1073* (2013.01); *A61B 5/1123* (2013.01); *A61B 5/6802* (2013.01); *A61B 5/725* (2013.01); *A61B 5/7264* (2013.01); *A61B 5/7275* (2013.01);

(Continued)

(58) Field of Classification Search

CPC ..................................................... G16H 50/30

See application file for complete search history.

(56) References Cited

U.S. PATENT DOCUMENTS

2026/0033789 A1* 2/2026 Goil .................... A61B 5/0006

OTHER PUBLICATIONS

Volkan Y. Senyurek et al., A CNN-LSTM neural network for recognition of pufng in smoking episodes using wearable sensors, Biomedical Engineering Letters, 2020, Korean Society of Medical and Biological Engineering, https://www.ncbi.nlm.nih.gov/pmc/articles/PMC7235127/pdf/13534_2020_Article_147.pdf.

(Continued)

*Primary Examiner* — Ajith Jacob

(74) *Attorney, Agent, or Firm* — Finnegan, Henderson, Farabow, Garrett & Dunner, LLP

(57) ABSTRACT

This disclosure relates generally to method and system for estimating smoking episodes from smoke puffs using a wearable device. Since the expense of treating diseases is rising, a digital smoking cessation improves healthcare systems such as cardiovascular issues. To achieve an optimum model given the platform limitations a very compact model is built specifically for the target microcontroller platform. The method of the present disclosure generates an optimum model for deployment on the wearable device using a pretrained deep neural network (DNN). A set of sensor signals are inputted to a convolutional neural network (CNN) smoke detection model to detect smoke puffs. Gesture classifier determines whether the user of the wearable device is engaged/engaging in a smoking session. Further, the method provides users of the wearable device with a cloud estimated smoking behavior analysis based on a set of smoking episodes to generate a set of user risk scores.

18 Claims, 9 Drawing Sheets

(51) Int. Cl.
*A61B 5/11* (2006.01)
*G16H 50/30* (2018.01)

(52) U.S. Cl.
CPC ...... *G16H 50/30* (2018.01); *A61B 2562/0219* (2013.01)

(56) References Cited

OTHER PUBLICATIONS

Amin Ahsan Ali, Automated Detection of Cigarette Smoking Puffs From Mobile Sensors—a Multimodal Approach, Dissertation, 2014, University of Memphis, https://digitalcommons.memphis.edu/cgi/viewcontent.cgi?article=2193&context=etd.

Narit Hnoohom et al., "An Efficient ResNetSE Architecture for Smoking Activity Recognition from Smartwatch," Intelligent Automation & Soft Computing, 2023, Tech science Press, https://www.techscience.com/iasc/v35n1/48175/pdf.

* cited by examiner

METHOD AND SYSTEM TO ESTIMATE SMOKING EPISODES FROM SMOKE PUFFS USING A WEARABLE DEVICE

PRIORITY CLAIM

This U.S. patent application claims priority under 35 U.S.C. § 119 to: Indian Patent Application No. 202321016334, filed on Mar. 11, 2023. The entire contents of the aforementioned application are incorporated herein by reference.

TECHNICAL FIELD

The disclosure herein generally relates to estimating smoking behavior analysis, and, more particularly, to method and system to estimate smoking episodes from smoke puffs using a wearable device.

BACKGROUND

Internet of Things (IOT) is a technology that has gained popularity and is essential to the development of smart city applications for disease. Smoking is a serious health issue that affects everyone in the world and has a negative impact on the economy. Smoking cessation is an important health practice because smoking causes health problems related to cancer, cardiovascular disease, high blood pressure and diabetes. Smoke patterns are analyzed as collections of time-discrete events to describe individual smoke series and reveal relationships between smoking and environmental events. When trying to quit smoking, it's important to be aware of your smoke puffs.

Conventional smoke detection methods detect smoke but are slower than deep learning methods in efficiency. Machine learning (ML) methods require subjective judgment to extract features and lack large-scale data to support the diversity of smoke features occurring at different times in different environments. Since the introduction of convolutional neural networks (CNNs), many approaches using deep learning convolutional neural networks have also emerged for smoke detection. Machine learning (ML) algorithms require prior feature extraction, so deep neural networks (DNNs) handle this in the model. DNNs can process large, high-dimensional datasets such as images, video, audio, and text. Deep learning has dramatically reduced the time to develop machine learning models for problems in various domains where sufficient labeled data is available. This is due to the automation of feature detection and engineering, which requires expertise. Smoke detection tends to apply emerging technologies where the DNN design process becomes non-trivial when additional constraints of embedded systems need to be met beyond the primary goal of generating an accurate model. However, because real-time smoke detection requires trained edge devices, existing methods are limited to estimating smoke behavior in the cloud. This is because sending raw data to the cloud drains the edge device's battery.

SUMMARY

Embodiments of the present disclosure present technological improvements as solutions to one or more of the above-mentioned technical problems recognized by the inventors in conventional systems. For example, in one embodiment, a method to estimate smoking episodes from smoke puffs using a wearable device—is provided. The method includes sending a set of wearable device hardware configurations to a pretrained deep neural network (DNN) to generate an optimal model for deployment on the portable device. Additionally, a set of sensor signals is collected from a set of sensors attached to the user. The set of sensor signals includes respiratory inductance photoplethysmogram (RIP) sensors, which measure the circumference of the user's chest and abdomen, and inertial sensors, which measure movement of the user's inertial data. A set of smoke gestures is presented to the wearable device and recognized by a set of sensors using a convolutional neural network (CNN) smoke detection models. Smoke gesture classification is performed on the set of sensor signals indicative of at least one smoke gesture, and whether the user of the wearable device participates in a smoking session based on the at least one smoke gesture classification including smoke puff and non-smoke puff. A smoking episode technique evaluates a number of puffs indicated by the user based on the classification of the smoking gesture, the frequency associated with one or more cigarettes, and the duration of one or more cigarettes associated with one or more cigarettes. Further, a set of smoking episodes are estimated to determine a total number of smoke puff(s). In addition, the cloud estimates smoking behavior analysis based on a set of smoking episodes and generate a set of risk scores provided to the user wearable device.

In another aspect, a system for method and system to estimate smoking episodes from smoke puffs using a wearable device is provided. The system includes sending a set of wearable device hardware configurations to a pretrained deep neural network (DNN) to generate an optimal model for deployment on the portable device. Additionally, a set of sensor signals is collected from a set of sensors attached to the user. The set of sensor signals includes respiratory inductance photoplethysmogram (RIP) sensors, which measure the circumference of the user's chest and abdomen, and inertial sensors, which measure movement of the user's inertial data. A set of smoke gestures is presented to the wearable device and recognized by a set of sensors using convolutional neural network (CNN) smoke detection models. Smoke gesture classification is performed on the set of sensor signals indicative of at least one smoke gesture, and whether the user of the wearable device participates in a smoking session based on the at least one smoke gesture classification including smoke puff and non-smoke puff. A smoking episode technique evaluates a number of smoke puffs indicated by the user based on the classification of the smoking gesture, the frequency associated with one or more cigarettes, and the duration of one or more cigarettes associated with one or more cigarettes. Further, a set of smoking episodes are estimated to determine a total number of smoke puff(s). In addition, the cloud estimates smoking behavior analysis based on a set of smoking episodes and generate a set of risk scores provided to the user wearable device.

In yet another aspect, a non-transitory computer readable medium for sending a set of wearable device hardware configurations to a pretrained deep neural network (DNN) to generate an optimal model for deployment on the portable device. Additionally, a set of sensor signals is collected from a set of sensors attached to the user. The set of sensor signals includes respiratory inductance photoplethysmogram (RIP) sensors, which measure the circumference of the user's chest and abdomen, and inertial sensors, which measure movement of the user's inertial data. A set of smoke gestures is presented to the wearable device and recognized by a set of sensors using a convolutional neural network (CNN) smoke detection models. Smoke gesture classification is performed on the set of sensor signals indicative of at least one smoke gesture, and whether the user of the wearable device participates in a smoking session based on the at least one smoke gesture classification including smoke puff and non-smoke puff. A smoking episode technique evaluates a number of puffs indicated by the user based on the classification of the smoking gesture, the frequency associated with one or more cigarettes, and the duration of one or more cigarettes associated with one or more cigarettes. Further, a set of smoking episodes are estimated to determine a total number of smoke puff(s). In addition, the cloud estimates smoking behavior analysis based on a set of smoking episodes and generate a set of risk scores provided to the user wearable device.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
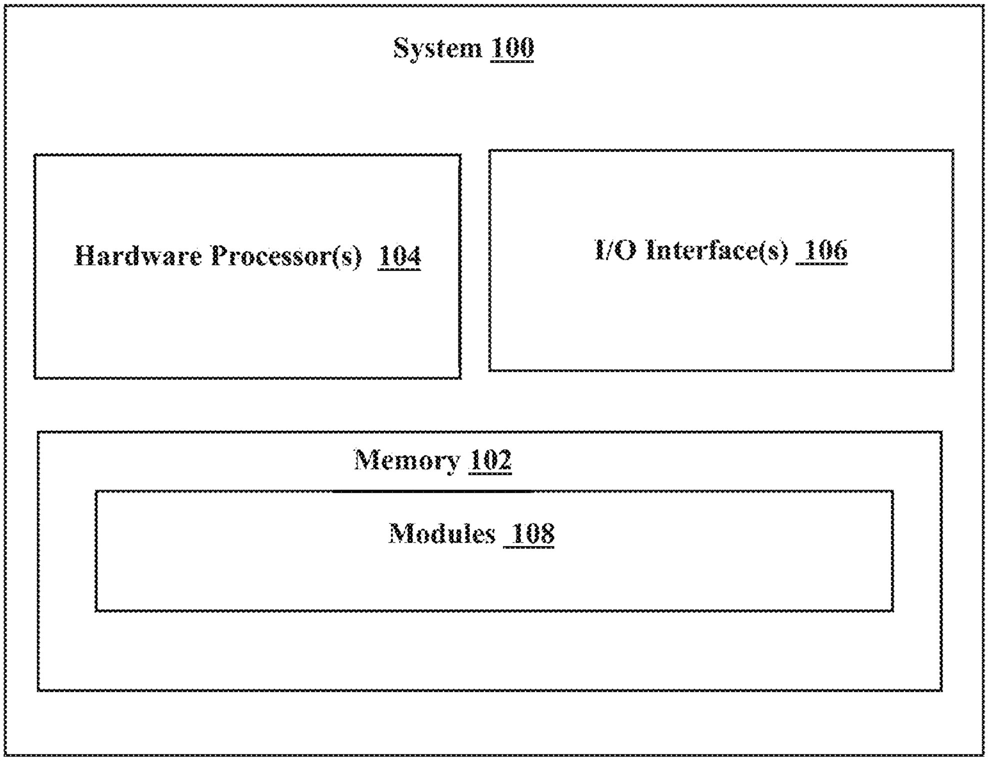
FIG. 1 is an exemplary method to estimate smoking episodes from smoke puffs using a wearable device, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Smoking has been conclusively proved to be the leading cause of mortality that accounts for one in five deaths. Given the adverse impact of smoking on human health, significant research is conducted on development of smoking interventions. Extensive research is conducted on developing effective smoking cessation programs. Identification of high-risk situations that may lead to an abstinent smoker involving discovery of the associations among various contexts that precede a smoking session. In the absence of an automated method, detection of smoking events still relies on user self-report that is prone to failure to report. Automated detection of smoking events in the natural environment can revolutionize smoking research and lead to effective intervention.

Embodiments herein provide a method and system to estimate smoking episodes from smoke puffs using a wearable device. The method disclosed, enables estimating smoking episodes using the wearable device of a user. The disclosed method provides Deep Q-Learning Neural Architecture Search (DQL-NAS) to generate optimal models suitable for user wearable devices. The best model is a reduced-size model built on a set of wearable device hardware configurations. The method disclosed also estimates a user's smoking behavior analysis based on a set of smoking episodes from a set of sensor signals. In particular, the wearable device may include a set of sensors and a gesture classifier trained to recognize at least one smoking gesture based on the output of the set of sensor signals. The disclosed method significantly improves smoke cloud detection accuracy for various configurations of handheld devices. The disclosed system is further explained with the method as described in conjunction with FIG. 1 to FIG. 7B below.

Referring now to the drawings, and more particularly to FIG. 1 through FIG. 7B, where similar reference characters denote corresponding features consistently throughout the figures, there are shown preferred embodiments, and these embodiments are described in the context of the following exemplary system and/or method.

FIG. 1 is an exemplary method to estimate smoking episodes from smoke puffs using a wearable device, according to some embodiments of the present disclosure. In an embodiment, the system 100 includes processor (s) 104, communication interface (s), alternatively referred as or input/output (I/O) interface(s) 106, and one or more data storage devices or memory 102 operatively coupled to the processor (s) 104. The system 100, with the processor(s) is configured to execute functions of one or more functional blocks of the system 100.

Referring to the components of the system 100, in an embodiment, the processor (s) 104 can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the processor(s) 104 is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud, and the like.

The I/O interface(s) 106 can include a variety of software and hardware interfaces, for example, a web interface, a graphical user interface, and the like and can facilitate multiple communications within a wide variety of networks and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server.

The memory 102 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. The memory 102 may comprise information pertaining to input(s)/output(s) of each step performed by the processor(s) 104 of the system 100 and methods of the present disclosure. Functions of the components of system 100, to estimate smoking episodes are explained in conjunction with FIG. 2 and FIG. 3 providing flow diagram, architectural overviews, and performance analysis of the system 100.

Figure 2:
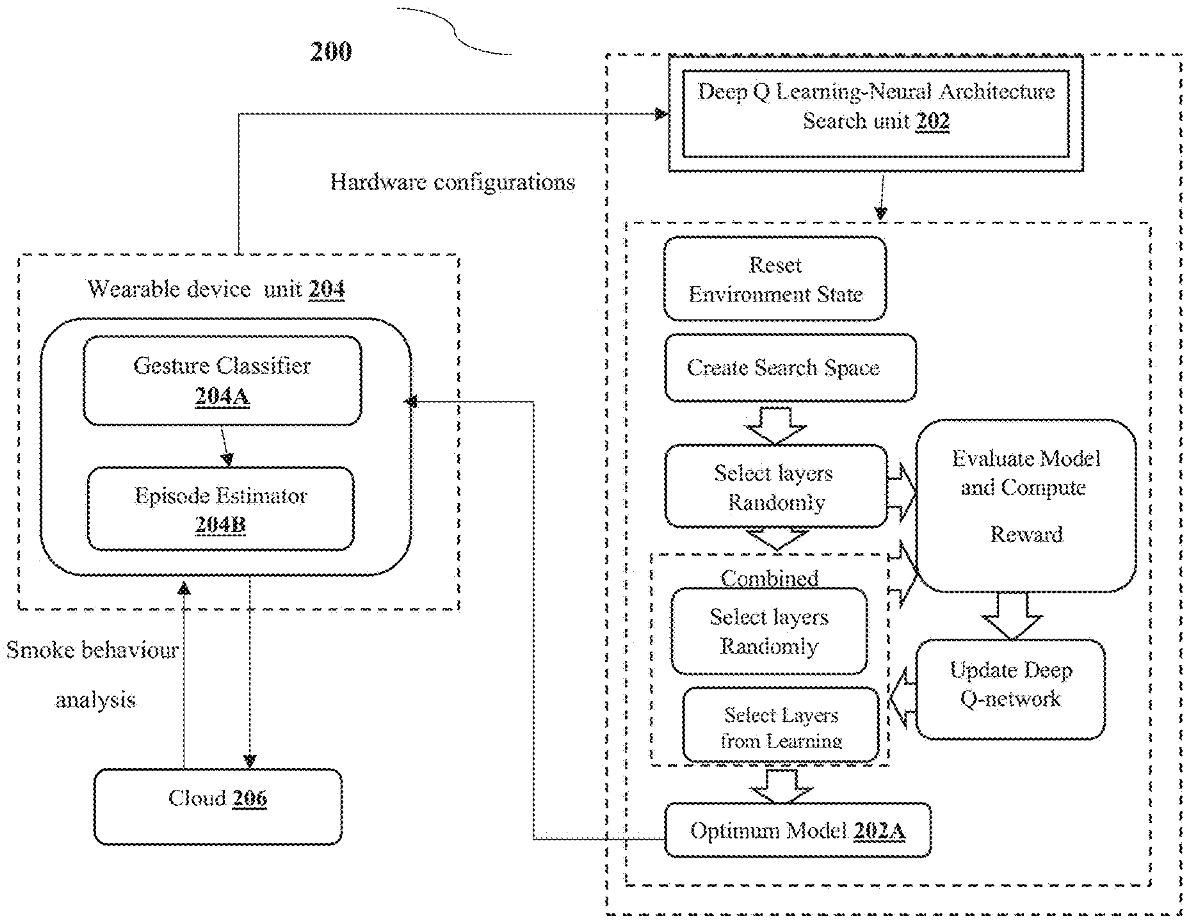
FIG. 2 is a functional block diagram showing components of a Deep Q-Learning Neural Architecture Search (DQL-NAS) using the system of FIG. 1, in accordance with some embodiments of the present disclosure.

FIG. 2 is a functional block diagram showing components of a Deep Q-Learning Neural Architecture Search (DQL-NAS) using the system of FIG. 1, in accordance with some embodiments of the present disclosure. The FIG. 2 includes a plurality of components comprising a Deep Q-Learning Neural Architecture Search (DQL-NAS) unit 202, a wearable device unit 204, and a cloud 206.

The Deep Q-Learning Neural Architecture Search unit 202 is a part of a deep neural network (DNN). The DQL-NAS unit 202 obtains a set of hardware configurations of the user wearable device to generate an optimum model 202A.

The wearable device unit 204 includes a gesture classifier 204A and an episode estimator 204B embedded in the user wearable device. The user wearable device may include a set of sensors that capture a set of sensor signals. For example, the set of sensors may include respiratory inductance photoplethysmogram (RIP) sensors and inertial sensors or other types of sensors. A set of sensor signals obtained from a set of sensors are processed to detect smoke clouds presented by the user.

Gesture classifier 204A processes the set of sensor signals before being inputted to subsequent components of system 100. The gesture classifier 204B indicates the type of gesture performed by the user based on the orientation of the wearable device. A calibration input helps to accurately identify the orientation of the wearable device.

Episode estimator 204B estimates a set of smoking episodes to identify a total number of smoke puffs exhibited by the user.

The cloud 206 estimates a smoking behavior analysis of the user by generating a set of risk scores. Smoke patterns from the smoking behavior analysis help characterize individual smoke series.

Figure 3:
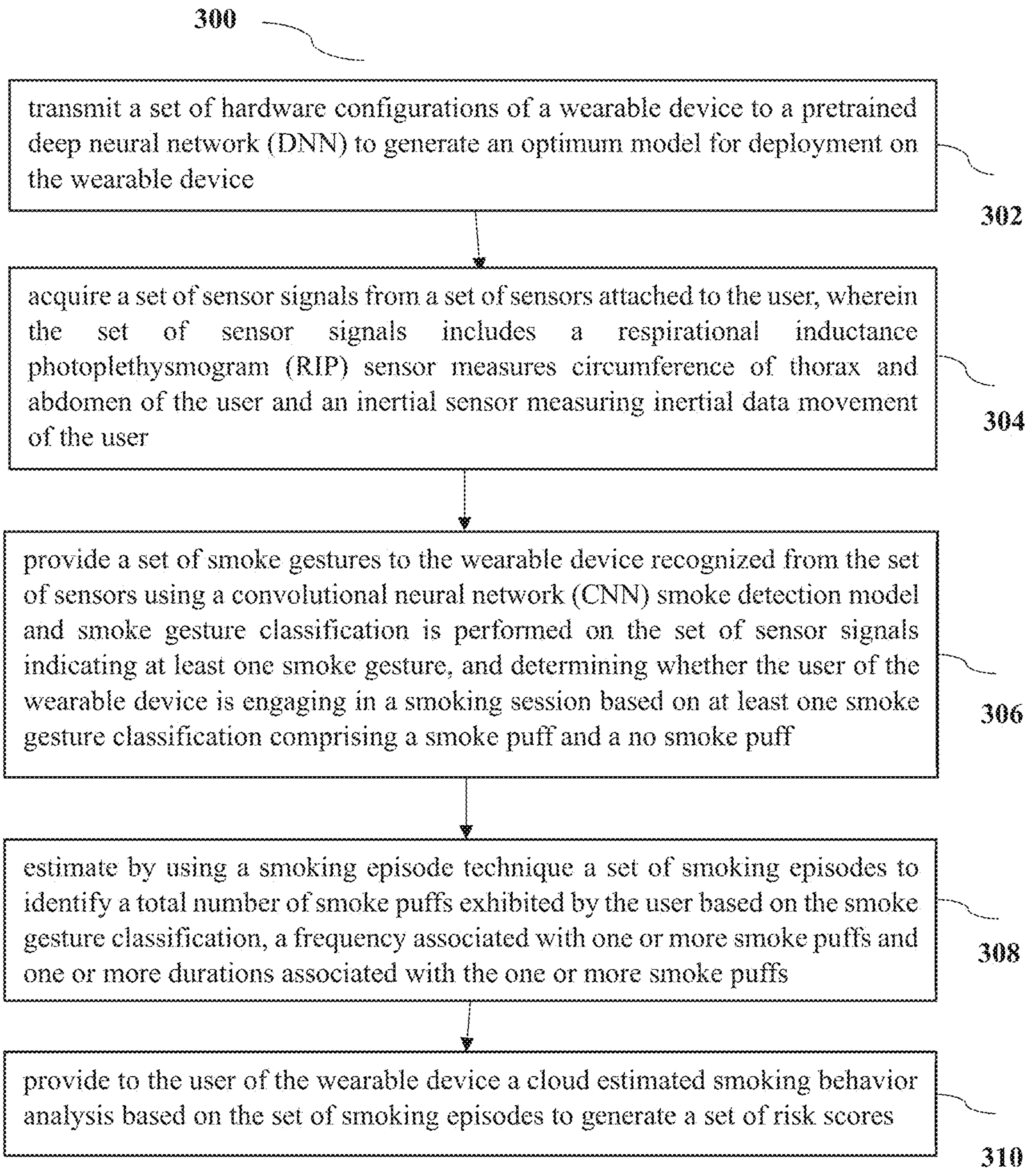
FIG. 3 is an exemplary flow diagram of a processor-implemented method to estimate smoking episodes using the system of FIG. 1, in accordance with some embodiments of the present disclosure.

FIG. 3 is an exemplary flow diagram of a processor-implemented method to estimate smoking episodes using the system of FIG. 1, in accordance with some embodiments of the present disclosure. In an embodiment, the system 100 comprises one or more data storage devices or the memory 102 operatively coupled to the processor(s) 104 and is configured to store instructions for execution of steps of the method 300 by the processor(s) or one or more hardware processors 104. The steps of the method 300 of the present disclosure will now be explained with reference to the components or blocks of the system 100 as depicted in FIG. 1 through FIG. 2 and the steps of flow diagram as depicted in FIG. 3. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring now to the steps of the method 300, at step 302, the one or more hardware processors 104 transmit a set of hardware configurations of a wearable device to a pretrained deep neural network (DNN) to generate an optimum model 202A for deployment on the wearable device.

For example, a pretrained deep neural network is embedded in the Deep Q-Learning Neural Architecture Search (DQL-NAS) unit 202 of the system 100 to automatically generate the optimum reduced-size model suitable for use on a suitable portable device. Generate. The Deep Q-Learning Neural Architecture Search unit 202 takes as input a set of wearable device hardware configurations and creates an appropriate network architecture according to the capacity of the wearable device. For example, the wearable device may include a watch, fitness tracker and the like.

The wearable device hardware configurations size may be 512 KB, 256 KB, and 100 KB to generate the optimum model 202A. In addition, DQL-NAS unit 202 has a state space that is the set of all possible deep neural network (DNN) layers and operations and all possible parameters defined. A DQL agent of the DQL-NAS traverses the state space using random layer selections called actions and a reward is assigned for every action performed by the DQL agent. Then, as learning progresses, the proportion of these random actions decreases and the DQL agent begins executing actions based on the pre-stored history database, further dynamic training of the DQL NAS unit 202 is performed to increase accuracy.

The efficiency of the chosen continuous layers and the generated optimal model 202A is quantified by the reward that combines all the desired metrics of the network. Once a layer is selected and the specified maximum depth is reached, the model is trained and scored to compute rewards for actions taken by the DQL agent. The reward is represented by Equation 1 which is a function of the series of multiply-accumulate operations (MACCS) related to model accuracy, size, and deep neural network (DNN) evaluation.

$$R = f_n(A, (S - S_t), (M - M_t)) \qquad \text{Equation 1}$$

Where $S_t$ and $M_t$ are thresholds for the depending on hardware specifications of the wearable device in focus while accuracy is a constant requirement for all application scenarios. The wearable device size and MACCS are heavily constrained depending on the focus hardware. For example, implementation have used the Arduino Nano 33 BLE board, a highly constrained platform with a RAM size of 256 KB. The reward expression helps the optimum model 202A that can be run on the wearable device at the same time and performs accurately within an acceptable range of accuracy drop.

At step 304 of the method 300, the one or more hardware processors 104 acquire a set of sensor signals from a set of sensors of the wearable device, wherein the set of sensor signals includes a respirational inductance photoplethysmogram (RIP) sensor that measures chest and waist circumferences and identifies changes in chest circumference caused by smoking and naturally occurring breathing. Inertial sensor captures accelerometer data in three physical directions in three physical dimensions.

In one implementation, the dataset was gathered and made public via the wearable called a Personal Automatic Cigarette Tracker (PACT). Inertial sensor records 6-axis inertial movements that record hand movements. The respirational inductance photoplethysmogram (RIP) measures the circumference of the chest or abdomen and conveys the expansion and contraction of the chest during smoking and natural breathing, captured by the chest band in the free-living state. This method further identifies nine variables recorded at 100 Hz in free-air smoking. The puff annotation for 40 people (no demographic information) is 1 for puffs and 0 for non-puffs for each sample (example eating, sleeping, going out), reading, and thereof). A typical puff lasts 10±8 seconds, and some puffs are long enough, such as 40 or 150 seconds.

At step 306 of the method 300, the one or more hardware processors 104 provide a set of smoke gestures to the wearable device recognized from the set of sensors using a convolutional neural network (CNN) and gesture classification is performed on the set of sensor signals indicating at least one smoke gesture, and the system 100 determines whether the user of the wearable device is engaging in a smoking session based on at least one smoke gesture classification comprising a smoke puff and a no smoke puff.

For example, the convolutional neural network (CNN) can be either a neural network or a linear network. Neural network(s) may include deep neural networks, feedforward neural networks, recurrent neural networks (e.g., long short-term memory recurrent neural networks), convolutional neural networks, or combinations thereof. The neural network has a total of four blocks: two convolutions and two squeeze-and-excitation (SE) blocks. A first squeeze-and-excitation block has a layer of 2D convolutions, followed by batch normalization, modified linear units (ReLU) as activations, and max pooling. A second squeeze-and-excitation block has two 2D convolutional layers, each followed by batch normalization and ReLU, and finally max pooling. The convolutional layer has 32 filters, each approximately 3×3 wide. At the end of each block there are two dropouts with probabilities of approximately 0.2 and 0.5 respectively. The last two blocks are serial squeeze-and-excitations. The first squeeze-and-excitation block receives both inputs from the second convolution block, the second SE block receives one input from the first SE block, and the other input from the first convolution block. The first squeeze-and-excitation block uses global average pooling to compress each channel to a single number, a fully connected layer backed by ReLU to provide the desired nonlinearity, a smooth gating function with a second fully connected layer, and sigmoidal activation. The result of this convolutional neural network (CNN) weight feature map in the convolution block. The second squeeze-and-excitation block provides the benefits of a content-aware approach while creating an output feature map that adaptively weights each channel, in contrast to CNNs that weight each channel equally. In addition, the first squeeze-and-excitation improves channel interdependence with minimal computation by adding a single parameter and a linear scalar to each channel to determine its relevance. Both inputs of the first squeeze-and-excitation block are outputs of the second convolution block.

In one embodiment, the set of sensor signals is input to the convolutional neural network (CNN) to recognize a set of smoking gestures. The set of sensor signals is acquired for each first interval of successive sections. For example, the first interval may contain 1000 samples. Additionally, the respiratory inductance photoplethysmogram (RIP) sensor signal, which measures arteriosclerosis, is processed using a Gaussian smoothing technique. The cutoff frequencies are 0.25 Hz acceleration and 0.15 Hz angular velocity. The inertial sensor signal, which measures the motion of the inertial data, is filtered using a second-order Butterworth lowpass filter. Additionally, resampling is performed to determine if the set of sensor signals indicates the presence of at least one smoking gesture, and each smoking gesture is analyzed for an optimal model of the user-wearable device.

As an example, gesture classifier 204A of system 100 classifies the detected sensor signal as a smoking gesture. The smoke gesture is either "smoke puff" or "no smoke puff". A "smoke puff" is identified from the set of sensor signals for further processing by episode estimator 204B. Each smoking gesture in the second interval is used to determine that the user is participating in a smoking session. For example, the second interval can be 10 seconds.

Smoking in a continuous segment is an episode or session that takes place while consuming a cigarette. At the same time, a "smoke puff" is a sequence of actions that begins with moving hand to mouth, inhaling, holding the smoke, exhaling, and moving hand away from mouth. The region between the two puffs is referred as "no smoke puff". Recognizing puffs is important for detecting smoking episodes or estimating a user's number of cigarettes per day. In the first subsystem, a specialized CNN-based network for puff detection to reduce the network by structured pruning of resource-constrained devices and use DQL-NAS unit 202 to construct a small model for deployment is automatically generated.

At step 308 of the method 300, the one or more hardware processors 104 estimate, by using a smoking episode technique, a set of smoking episodes to identify a total number of smoke puffs exhibited by the user based on the smoke gesture classification, a frequency associated with one or more smoke puffs and one or more durations associated with the one or more smoke puffs.

The episode estimator 204B can receive all outputs from the gesture classifier 204A. The accuracy of episode estimator 204B of daily cigarette count is of higher clinical significance than individual smoke puffs. However, the Personal Automatic Cigarette Tracker (PACT) data does not provide annotations for the episodes. Timestamps of the set of sensor signals helps to create data. Smoking analyses say that the average time consuming one cigarette is around (5 to 10) minutes. For all continuous smoking data in the range (10±5) minutes associated with (20±5) number of puffs as one episode and validate it with the detected puffs using the smoking episode technique (referring now to Table 1)

The episode estimator 204B may receive the entire output of the gesture classifier 204A. The accuracy of the episode estimator 204B of daily cigarette count is of higher clinical significance than individual smoke puffs. However, the PACT data do not contain episodic annotations. Time stamps of the series of sensor signals are useful for data creation. According to smoke behavior analysis, the average time it takes to smoke a cigarette is about (5-10) minutes. Validation with all continuous smoking data ranging from (10±5)

minutes associated with (20±5) puffs as one episode and puffs detected using the smoking episode technique (Referring to Table 1)

TABLE 1

| Smoking episode technique |
|---|
| Procedure ESTIMATE EPISODES ($P_c$,t) |
| $E_{num} = 0, C_1 = 0, C_2 = 0$ |
| For $i = t_{start}$ to $t_{stop}$ do |
| If $P_c i \geq TH_1$ then |
| $C_1 = C_1 + 1$ |
| If $P_c i \geq TH_2$ then |
| $C_2 = C_2 + 1$ |
| If $LLC_1 \leq C_1 < ULC_1$ and $LLC_2 \leq C_2 < ULC_2$ then |
| $E_{num} = E_{num} + 1$ |
| $C_1 = 0$ |
| $C_2 = 0$ |
| Return $E_{num}$ |

The smoking episode technique extracts a set of parameters comprising an episode number $E_{num}$, a first count $C_1$, and a second count $C_2$ and each smoking episode for a selected duration (time interval between $t_{start}$ and $t_{stop}$) from the smoke puff confidences $P_c$. Here, the first count $C_1$ and the second count $C_2$ represents the counts when the puff confidences $P_c$ exceeds a chosen a first threshold $TH_1$ and a second threshold $TH_2$ respectively. Further, a lower limit $LLC_1$ has a range for the first count $C_1$ and an upper limit $ULC_1$ specify the range for the second count $C_2$.

For example, the first count is incremented when the puff confidence value at every event interval is greater than or equal to the first threshold $TH_1$. Then, the second count is incremented when the puff confidence value at every event interval is greater than or equal to the second threshold $TH_2$. The episode number is incremented and the first count $C_1$ and the second count $C_2$ are reset if (i) the first count falls between the lower limit of the first count and the upper limit of the first count and (ii) the second count falls between the lower limit of the second count and the upper limit of the second count.

If the accuracy of puff detection is x % (example, 80%), then the first threshold is at 80th percentile and the second threshold $TH_2$ is approximately at $(1-TH_1)$, which is y % (example, 20%). In such scenario, selecting the first count $C_1$ which is the minimum number of puff confidences at least present in the first threshold (80th percentile) and its range $LLC_1$ and $ULC_1$, can be set heuristically. Similarly, the lower and upper limits can be set for the second count $C_2$ which is the minimum number of puff confidences at least present in the second threshold $TH_2$.

At step 310 of the method 300, the one or more hardware processors 104 provide, a smoking behavior analysis estimated by a cloud, to the user of the wearable device based on the set of smoking episodes and generating a set of risk scores for the user. Here, nudges can be sent to the wearable device of the user based on analysis of smoking behavior performed in the cloud. Cigarette counts estimated by mobile device(s) can help generate a set of risk scores for all smoking-related diseases and can be further analyzed to optimize personalized reminders for the user. This is further helpful in presenting the probability of smoking death at different ages in light and heavy smokers and ex-smokers. Considering Table 2, men who smoked 25 or more cigarettes a day from age 35 to age 44 (C/D) had a 28.3% relative risk of dying before age 75.

TABLE 2

| Death risk before the age of 75 years | | |
|---|---|---|
| Cause of Death | (<25 cigarettes per day) | (Above 25 cigarettes per day) |
| Lung cancer | 6.3 | 13 |
| Coronary heart disease | 7.4 | 10.2 |
| All smoking related disorders | 16.9 | 28.3 |

In Table 2, there are two categories, smokers consuming less than 25 cigarettes per day (C/D) and smokers consuming more than equals 25 C/D. Similarly, we can categorize light and heavy smoking based on the requirement and warn the user if the limit is exceeded.

Figure 4:
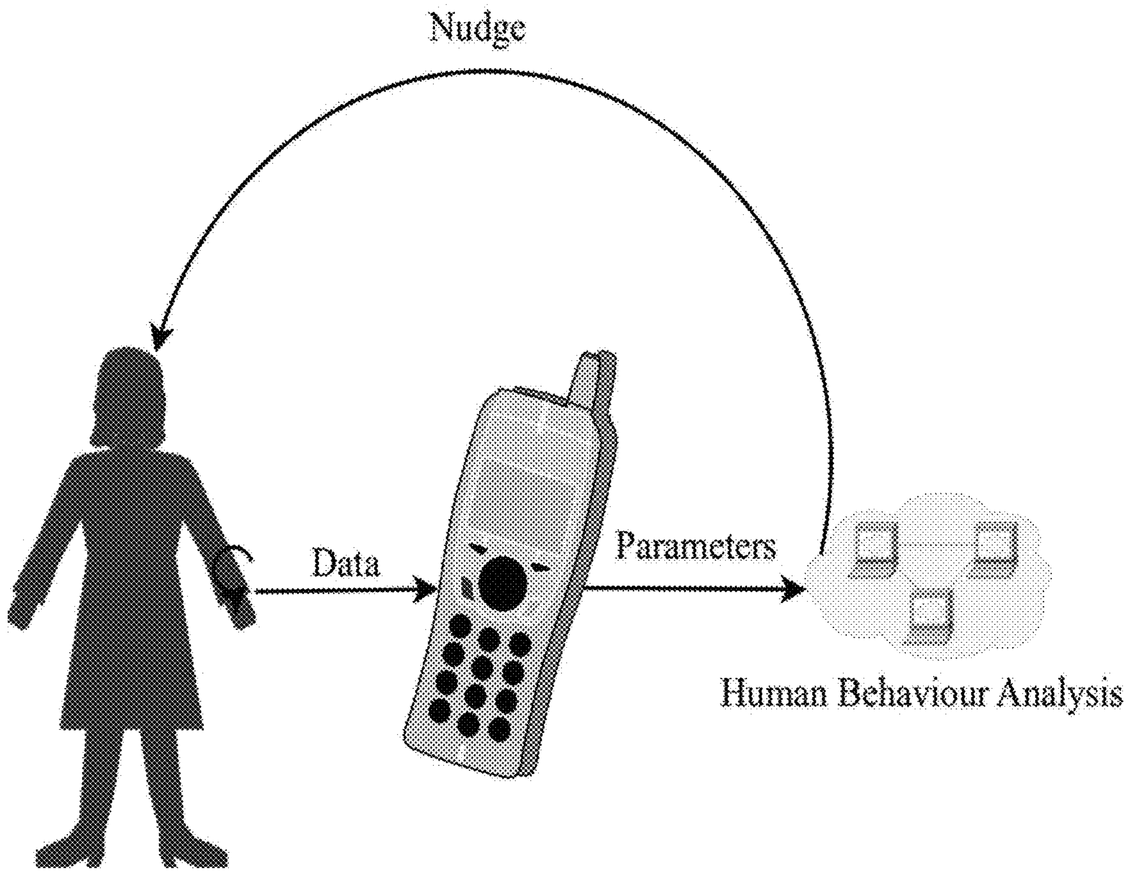
FIG. 4 is an example user connected to a wearable device that can estimate smoking episodes using the system of FIG. 1, in accordance with some embodiments of the present disclosure.

FIG. 4 is an example user connected to a wearable device that can estimate smoking episodes using the system of FIG. 1, in accordance with some embodiments of the present disclosure. The example system architecture shown in FIG. 4 consists of three sub-systems (i) the wearable device, (ii) the user mobile device, and the (iii) cloud. From the wearable device, the "puffs" are detected and provided to the mobile using a wireless technology. From the mobile, a mobile broadband is used to send the set of episodes (cigarette counts) to the cloud. The cloud then computes a smoking behavior for the user and provides personalized nudges.

Figure 5A:
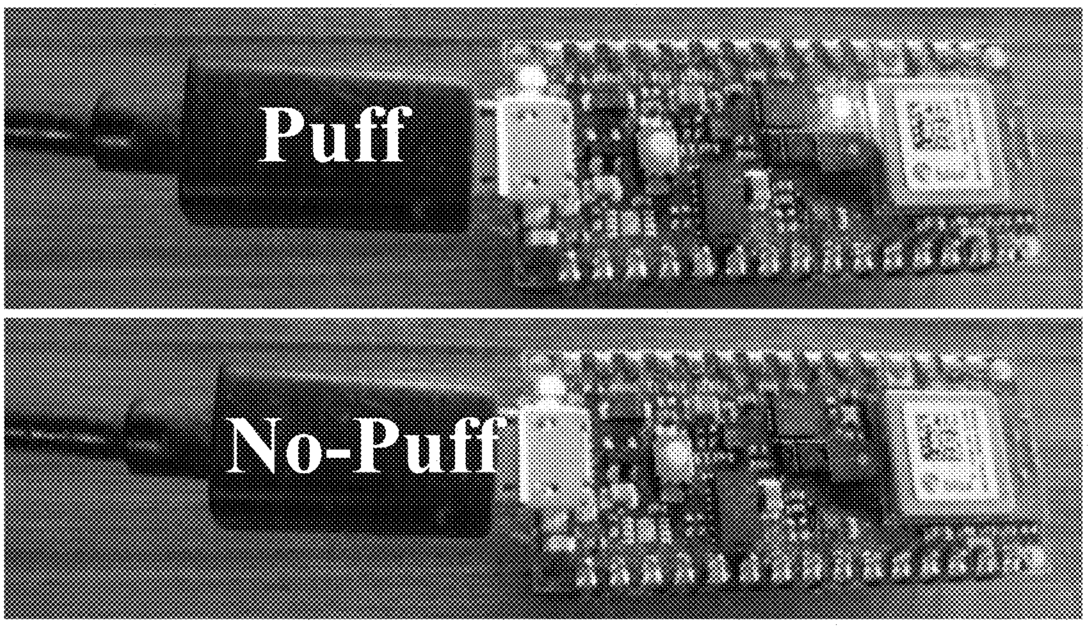
FIG. 5A is an example model implementation on Arduino Nano 33 Bluetooth low energy (BLE) using the system of FIG. 1, in accordance with some embodiments of the present disclosure.

FIG. 5A is an example model implementation on Arduino Nano 33 Bluetooth low energy (BLE) using the system of FIG. 1, in accordance with some embodiments of the present disclosure. FIG. 5A describes the two auto-generated models with target sizes 100 KB and 256 kB, respectively, have been deployed on the wearable device representing the results actuated. The smallest model (64.26 KB size) utilizes 182.3 KB Flash memory on the device, and a peak RAM usage of 220.1 KB at runtime, with an inference latency of 1.3 s. The second model (111.77 KB) utilizes 186.5 KB of Flash memory and a peak RAM usage of 231.3 kB, with an inference latency of 2.1 s.

On the Arduino Nano 33 Bluetooth Low Energy (BLE), model reduction provides precision-preserving pruning and quantization strategies to reduce optimal models. Due to quantization, the parametric representation in memory is changed from some kind of 32-bit floating point number (Float32) to an 8-bit integer (int8). By choosing the int8 format to fit the model in memory at the cost of up to 4% accuracy. This model was suitable for MCU flash but ran out of microcontroller static RAM or SRAM at runtime. This is because TensorFlow Lite Micro (TFLM), the framework used for model customization and execution, occupies considerable memory space along with the model.

Based on further experiments, the steps of the first convolutional layer are dramatically increased, reducing the number of parameters in the network without sacrificing accuracy. By truncating and quantizing this final model to generate a 250 kB model that could be effectively run in hardware, enabling on-device inference with only 1% accuracy loss over the base model. However, the above process requires a few trial and error iterations for another MCU with a slightly smaller flash memory (100 KB). In general, building models with different accuracy size trade-offs for different target platforms with different flash memory sizes and RAM is a tedious manual effort and deep learning-savvy resources. This further automates the task of generating custom DNN model for specific platform constraints (flash memory and RAM size) and application requirements (accuracy and inference latency). Therefore, an architectural search space is developed from the above models to automatically generate small resource-optimized models, eliminating the need for manual reduction and trial-and-error due to hardware limitations.

Figure 5B:
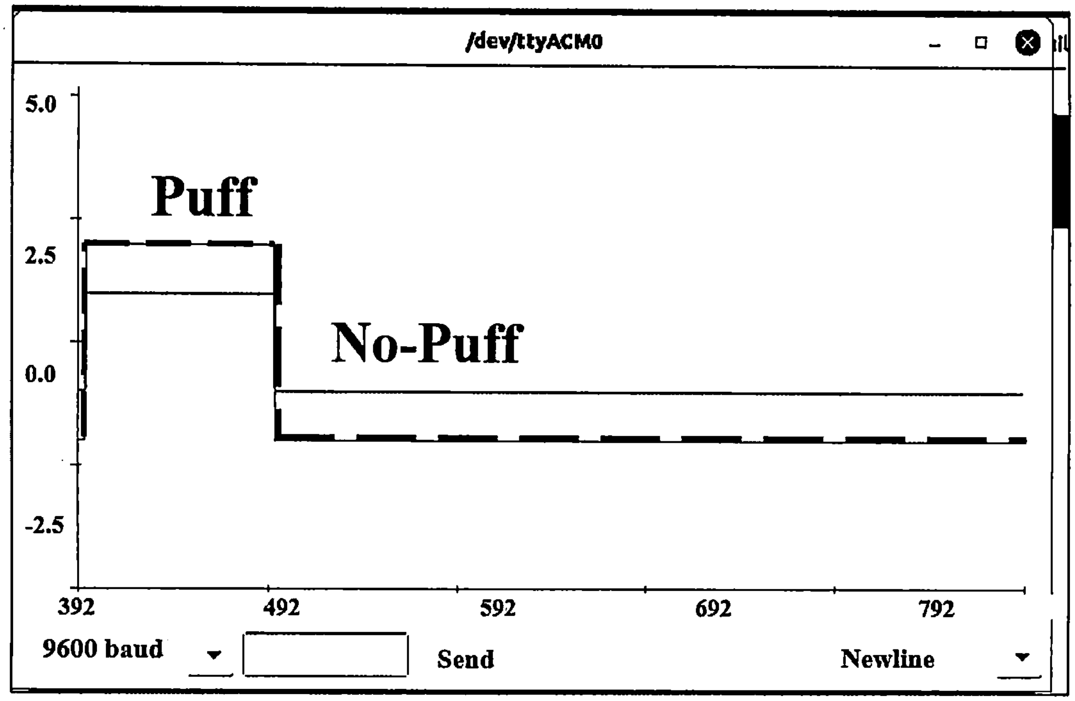
FIG. 5B is an example waveforms showing a smoke puff and a no smoke puff from a plurality of sensor signals using the FIG. 5A, in accordance with some embodiments of the present disclosure.

FIG. 5B is an example waveform showing a smoke puff and a no smoke puff from a plurality of sensor signals using the FIG. 5A, in accordance with some embodiments of the present disclosure. The optimum model 202A generated by the DQL-NAS unit 202 provides experimental results of three output models of size 247.79 KB, 111.77 KB, and 64.26 KB for target sizes 512 KB, 256 KB, and 100 kB, respectively. These experiments were performed over 3000 episodes of a reinforcement learning (RL) where 1500 episodes were reserved for random actions, denoted by an exploration rate ε parameter. The remaining combined random and learned actions depend on the ε, which decreases gradually from 1 to a minimum value of 0.1.

Figure 6:
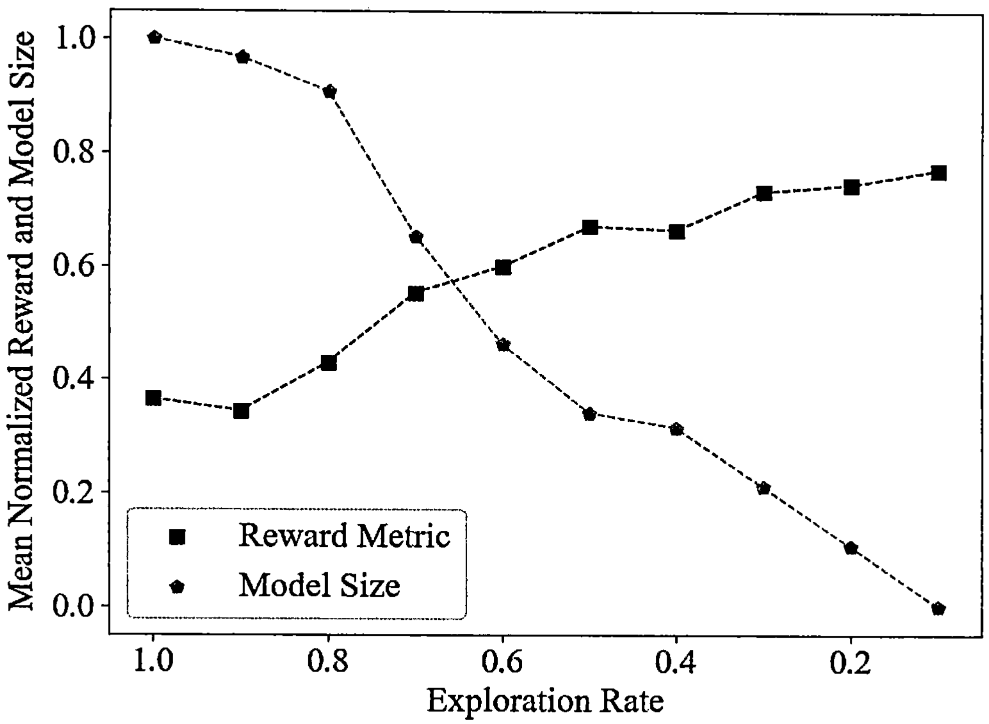
FIG. 6 is an optimum model generated by the Deep Q-Learning Neural Architecture Search (DQL-NAS) to be installed in the wearable device of a user using the system of FIG. 1, in accordance with some embodiments of the present disclosure.

FIG. 6 is an optimum model generated by the Deep Q-Learning Neural Architecture Search (DQL-NAS) to be installed in the wearable device of the user using the system 100 of FIGS. 1-2, in accordance with some embodiments of the present disclosure. FIG. 6 shows reward optimization and reduction of the optimum model 202A size, with the progress of episodes and decreasing ¿. The models present puff detection accuracy values of 79.8%, 76.9%, and 74.7% for the size constraints of 512 KB, 256 KB, and 100 KB, respectively, in rows 2-4 of Table 3, and Episode—Puff MAD comparison. In one embodiment, Table 3 represents the base model showing user fold-cross-validated averaged performance for puff detection.

TABLE 3

Performance Comparison of Base model with DQL-NAS generated optimum models

| Model | Accuracy | Sensitivity | Specificity | Precision | F1-Score | Size(KB) |
|---|---|---|---|---|---|---|
| Base | 79.2 ± 16 | 79.2 ± 18 | 79.2 ± 14 | 80.9 ± 15 | 81 ± 11 | 472.8 |
| DQL-NAS1 | 79.2 ± 9 | 78.8 ± 13 | 80.8 ± 15 | 82.4 ± 15 | 78 ± 12 | 247.79 |
| DQL-NAS2 | 76.9 ± 10 | 75.6 ± 14 | 79.7 ± 13 | 79.8 ± 16 | 75.2 ± 12 | 111.77 |
| DQL-NAS3 | 74.7 ± 10 | 71.8 ± 18 | 77.3 ± 18 | 79.8 ± 17 | 72.1 ± 14 | 64.26 |

With an accuracy of 79.2%, a false-negative rate of 21%, and a false discovery rate of 19%, an F1 score of 81% has been achieved. To estimate the number of episodes in each user, the puff confidences (PC) is computed and resampled with the time duration is the same as the original puff.

Figure 7A:
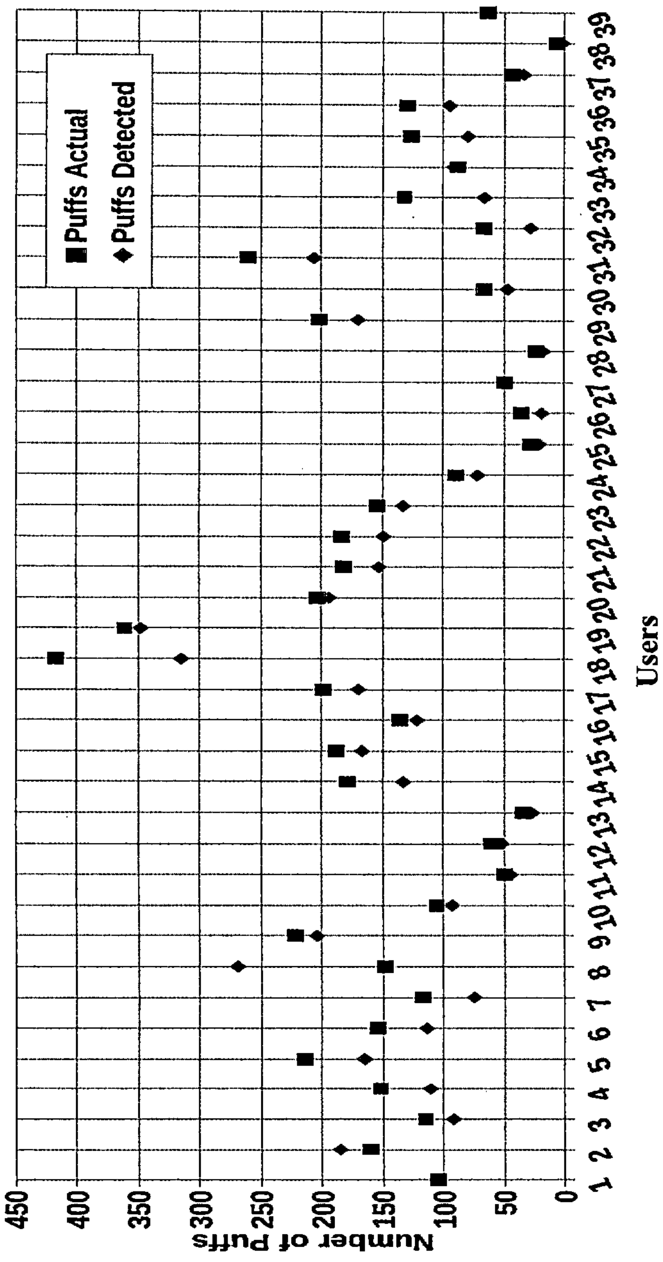
FIG. 7A is a graph showing a number of smoke puff exhaled by the user using the system of FIG. 1, in accordance with some embodiments of the present disclosure.

FIG. 7A is a graph showing a number of smoke puff exhaled by the user using the system of FIG. 1, in accordance with some embodiments of the present disclosure. FIG. 7A represents the number of smoke puff exhaled by the user depicting actual smoke puffs exhaled by the user and the number of false positives detected as smoke puffs.

Figure 7B:
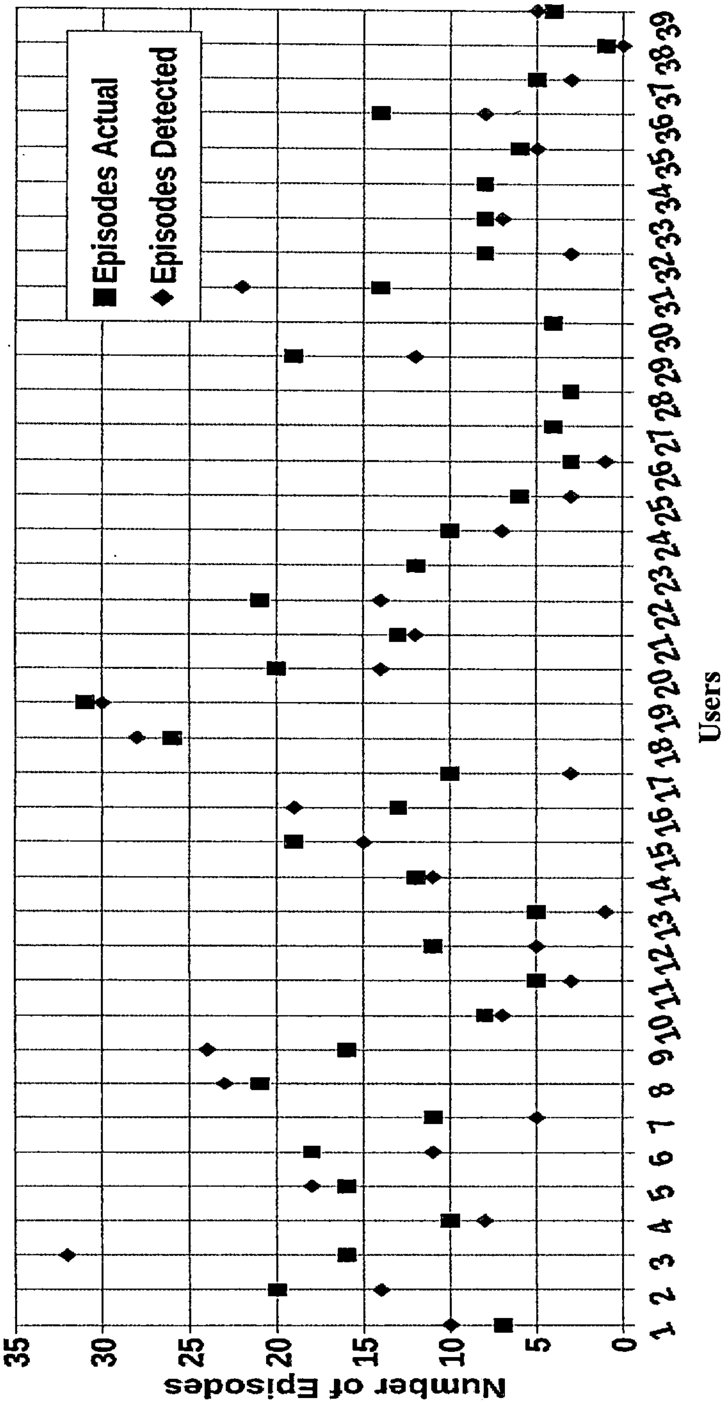
FIG. 7B is a graph showing the user's smoking behavior analysis of the user based on a set of smoking episodes using the system of FIG. 1, in accordance with some embodiments of the present disclosure.

FIG. 7B is a graph showing the user's smoking behavior analysis of the user based on a set of smoking episodes using the system of FIG. 1, in accordance with some embodiments of the present disclosure. FIG. 7B shows comparison of an original number of smoke "puffs" and each smoking episode of the user.

TABLE 4

Mean Absolute Deviation (MAD) for identified smoke puffs and smoke episodes

| | Actual | Base Model | | DQL-NAS1 (247.79 KB) | | DQL-NAS2 (111.77 KB) | | DQL-NAS3 (64.26 KB) | |
|---|---|---|---|---|---|---|---|---|---|
| | Count | Count | MAD | Count | MAD | Count | MAD | Count | MAD |
| Smoke Puffs | 5254 | 4482 | 26.1 | 4120 | 25.4 | 4102 | 31 | 3980 | 35.6 |
| Smoke Episodes | 458 | 414 | 3.41 | 385 | 3.53 | 400 | 3.61 | 364 | 4.34 |

-

Table 4 depicts the Mean Absolute Deviation (MAD) calculated for the identified "smoke puffs" and estimated episode for all 39 users to quantify the variation. As an outcome, a low value of 3.4 for the episode MAD compared to Puff which is 26. However, even if identifying the puffs are skipped, the episode count accurately and serve the objective of identifying a pack a day or a week or a month for a specific smoker.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of estimating smoking behavior analysis. The embodiment, thus provides method and system to estimate smoking episodes from smoke puffs using a wearable device. Moreover, the embodiments herein further provide a technique to quantify smoking episodes based on the likelihood of detected puffs is provided by a specialized convolutional Neural Network (CNN) for "puff" from Respirational Inductance Photoplethysmogram (RIP) with a 6-axis IMU signal, which achieved 81% F1-score. The optimum model 202A fits it to a single piece of target hardware using model reduction techniques, such as pruning, quantization, and intelligent data manipulation. The developing models with various accuracy-size tradeoffs for various target systems is frequently a laborious and brute-force task. The method of the present disclosure provides an end-to-end solution for online smoking detection for a use case including smoking cessation. Additionally, the optimum model 202A can be deployed via base DQL-NAS unit 202 on the typical wearable device. The episode detection accuracy is much higher than "puff" detection accuracy, which is a satisfactory level of accuracy for puff detection. This makes it easier to calculate a smoker's pack-per-day, which enables the application of the proper controls.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method to estimate smoking episodes from smoke puffs using a wearable device, comprising:

transmitting via one or more hardware processors, a set of hardware configurations of a wearable device to a pretrained deep neural network (DNN) to generate an optimum model for deployment on the wearable device;

acquiring via the one or more hardware processors, a set of sensor signals from a set of sensors attached to the user, wherein the set of sensor signals includes a respirational inductance photoplethysmogram (RIP) sensor measures circumference of thorax and abdomen of the user and an inertial sensor measuring inertial data movement of the user;

providing via the one or more hardware processors, a set of smoke gestures to the wearable device recognized from the set of sensors using a convolutional neural network (CNN) smoke detection model and smoke gesture classification is performed on the set of sensor signals indicating at least one smoke gesture, and determining whether the user of the wearable device is engaging in a smoking session based on at least one smoke gesture classification comprising a smoke puff and a no smoke puff;

estimating by using a smoking episode technique via the one or more hardware processors, a set of smoking episodes to identify a total number of smoke puffs exhibited by the user based on the smoke gesture classification, a frequency associated with one or more smoke puffs and one or more durations associated with the one or more smoke puffs; and providing to the user of the wearable device via the one or more hardware processors, a cloud estimated smoking behavior analysis based on the set of smoking episodes to generate a set of risk scores.

2. The processor implemented method as claimed in claim 1, wherein the set of sensor signals are inputted to the convolutional neural network (CNN) to recognize the set of smoke gestures by performing the steps of:

obtaining the set of sensor signals respectively at every first interval;

preprocessing the respirational inductance photoplethysmogram (RIP) sensor signals measuring circumference of thorax and abdomen using a gaussian smoothing technique and filtering the inertial sensor signals measuring the inertial data movement using a second-order low pass Butterworth filter;

analyzing the output of CNN to determine whether the set of sensor signals indicates the presence of at least one smoke gesture; and resampling each smoke gesture at a second interval to determine the user of the wearable device is engaging in the smoking session and transmitting each smoke gesture to the optimum model of the user wearable device.

3. The processor implemented method as claimed in claim 1, estimating a set of smoking episodes by using the smoking episode technique by performing the steps of:

initializing a set of parameters comprising an episode number, a first count, and a second count; and estimating each smoking episode between a start time interval and an end time interval by performing the steps of:

the first count is incremented when a puff confidence value at every event interval is greater than or equal to a first threshold, and the second count is incremented when the puff confidence value at every event interval is greater than or equal to a second threshold; and the episode number is incremented and reset the first count and the second count if the first count falls between a lower limit of the first count and an upper limit of the first count and the second count falls between the lower limit of the second count and the upper limit of the second count.

4. The processor implemented method as claimed in claim 1, wherein the cloud provides the user smoking behavior analysis by using a set of smoking episodes to generate a set of risk scores for at least one smoking-related disorder.

5. The processor implemented method as claimed in claim 1, wherein the smoking behavior analysis provides user with personalized reminders based on the set of risk scores.

6. The processor implemented method as claimed in claim 1, wherein the set of risk scores provides user probabilities of death from smoking at various ages.

7. A system 100 to estimate smoking episodes from smoke puffs using a wearable device comprising:

a memory storing instructions;

one or more communication interfaces; and one or more hardware processors coupled to the memory via the one or more communication interfaces, wherein the one or more hardware processors are configured by the instructions to:

transmit a set of hardware configurations of a wearable device to a pretrained deep neural network (DNN) to generate an optimum model for deployment on the wearable device;

acquire a set of sensor signals from a set of sensors attached to the user, wherein the set of sensor signals includes a respirational inductance photoplethysmogram (RIP) sensor measures circumference of thorax and abdomen of the user and an inertial sensor measuring inertial data movement of the user;

provide a set of smoke gestures to the wearable device recognized from the set of sensors using a convolutional neural network (CNN) smoke detection model and smoke gesture classification is performed on the set of sensor signals indicating at least one smoke gesture, and determining whether the user of the wearable device is engaging in a smoking session based on at least one smoke gesture classification comprising a smoke puff and a no smoke puff;

estimate by using a smoking episode technique a set of smoking episodes to identify a total number of smoke puffs exhibited by the user based on the smoke gesture classification, a frequency associated with one or more smoke puffs and one or more durations associated with the one or more smoke puffs; and provide to the user of the wearable device a cloud estimated smoking behavior analysis based on the set of smoking episodes to generate a set of risk scores.

8. The system as claimed in claim 7, wherein the set of sensor signals are inputted to the convolutional neural network (CNN) to recognize the set of smoke gestures by performing the steps of:

obtain the set of sensor signals respectively at every first interval;

preprocess the respirational inductance photoplethysmogram (RIP) sensor signals measuring circumference of thorax and abdomen using a gaussian smoothing technique and filtering the inertial sensor signals measuring the inertial data movement using a second-order low pass Butterworth filter;

analyze the output of CNN to determine whether the set of sensor signals indicates the presence of at least one smoke gesture; and resample each smoke gesture at a second interval to determine the user of the wearable device is engaging in the smoking session and transmitting each smoke gesture to the optimum model of the user wearable device.

9. The system as claimed in claim 7, estimating a set of smoking episodes by using the smoking episode technique by performing the steps of:

initialize a set of parameters comprising an episode number, a first count, and a second count; and estimate each smoking episode between a start time interval and an end time interval by performing the steps of:

the first count is incremented when a puff confidence value at every event interval is greater than or equal to a first threshold, and the second count is incremented when the puff confidence value at every event interval is greater than or equal to a second threshold; and the episode number is incremented and reset the first count and the second count if the first count falls between a lower limit of the first count and an upper limit of the first count and the second count falls between the lower limit of the second count and the upper limit of the second count.

10. The system as claimed in claim 7, wherein the cloud provides the user smoking behavior analysis by using a set of smoking episodes to generate a set of risk scores for at least one smoking-related disorder.

11. The system as claimed in claim 7, wherein the smoking behavior analysis provides user with personalized reminders based on the set of risk scores.

12. The system as claimed in claim 7, wherein the set of risk scores provides user probabilities of death from smoking at various ages.

13. One or more non-transitory machine-readable information storage mediums comprising one or more instructions which when executed by one or more hardware processors cause:

transmitting a set of hardware configurations of a wearable device to a pretrained deep neural network (DNN) to generate an optimum model for deployment on the wearable device;

acquiring a set of sensor signals from a set of sensors attached to the user, wherein the set of sensor signals includes a respirational inductance photoplethysmogram (RIP) sensor measures circumference of thorax and abdomen of the user and an inertial sensor measuring inertial data movement of the user;

providing a set of smoke gestures to the wearable device recognized from the set of sensors using a convolutional neural network (CNN) smoke detection model and smoke gesture classification is performed on the set of sensor signals indicating at least one smoke gesture, and determining whether the user of the wearable device is engaging in a smoking session based on at least one smoke gesture classification comprising a smoke puff and a no smoke puff;

estimating by using a smoking episode technique a set of smoking episodes to identify a total number of smoke puffs exhibited by the user based on the smoke gesture classification, a frequency associated with one or more smoke puffs and one or more durations associated with the one or more smoke puffs; and providing to the user of the wearable device a cloud estimated smoking behavior analysis based on the set of smoking episodes to generate a set of risk scores.

14. The one or more non-transitory machine-readable information storage mediums of claim 13, wherein the set of sensor signals are inputted to the convolutional neural network (CNN) to recognize the set of smoke gestures by performing the steps of:

obtaining the set of sensor signals respectively at every first interval;

preprocessing the respirational inductance photoplethysmogram (RIP) sensor signals measuring circumference of thorax and abdomen using a gaussian smoothing technique and filtering the inertial sensor signals measuring the inertial data movement using a second-order low pass Butterworth filter;

analyzing the output of CNN to determine whether the set of sensor signals indicates the presence of at least one smoke gesture; and resampling each smoke gesture at a second interval to determine the user of the wearable device is engaging in the smoking session and transmitting each smoke gesture to the optimum model of the user wearable device.

15. The one or more non-transitory machine-readable information storage mediums of claim 13, estimating a set of smoking episodes by using the smoking episode technique by performing the steps of:

initializing a set of parameters comprising an episode number, a first count, and a second count; and estimating each smoking episode between a start time interval and an end time interval by performing the steps of:

the first count is incremented when a puff confidence value at every event interval is greater than or equal to a first threshold, and the second count is incremented when the puff confidence value at every event interval is greater than or equal to a second threshold; and the episode number is incremented and reset the first count and the second count if the first count falls between a lower limit of the first count and an upper limit of the first count and the second count falls between the lower limit of the second count and the upper limit of the second count.

16. The one or more non-transitory machine-readable information storage mediums of claim 13, wherein the cloud provides the user smoking behavior analysis by using a set of smoking episodes to generate a set of risk scores for at least one smoking-related disorder.

17. The one or more non-transitory machine-readable information storage mediums of claim 13, wherein the smoking behavior analysis provides user with personalized reminders based on the set of risk scores.

18. The one or more non-transitory machine-readable information storage mediums of claim 13, wherein the set of risk scores provides user probabilities of death from smoking at various ages.

* * * * *